(12) United States Patent
De Nanteuil et al.

(10) Patent No.: US 7,265,220 B2
(45) Date of Patent: Sep. 4, 2007

(54) AMINO ACID DERIVATIVES, METHOD FOR PRODUCTION THEREOF AND PHARMACEUTICAL COMPOSITIONS COMPRISING SAID DERIVATIVE

(75) Inventors: Guillaume De Nanteuil, Suresnes (FR); Philippe Gloanec, Marly le Roy (FR); Tony Verbeuren, Vernouillet (FR); Alain Rupin, Savonnieres (FR)

(73) Assignee: Les Laboratories Servier, Courbevoie Cedex (FR)

( * ) Notice: Subject to any disclaimer, the term of this patent is extended or adjusted under 35 U.S.C. 154(b) by 349 days.

(21) Appl. No.: 10/505,005

(22) PCT Filed: Feb. 17, 2003

(86) PCT No.: PCT/FR03/00506

§ 371 (c)(1), (2), (4) Date: Aug. 18, 2004

(87) PCT Pub. No.: WO03/070690

PCT Pub. Date: Aug. 28, 2003

(65) Prior Publication Data

US 2005/0085517 A1    Apr. 21, 2005

(30) Foreign Application Priority Data

Feb. 21, 2002 (FR) .................. 02 02199

(51) Int. Cl.
| | |
|---|---|
| *C07C 257/18* | (2006.01) |
| *C07C 311/13* | (2006.01) |
| *C07C 311/19* | (2006.01) |
| *C07C 259/18* | (2006.01) |
| *A61K 31/196* | (2006.01) |
| *A61P 7/04* | (2006.01) |
| *C07D 213/34* | (2006.01) |
| *C07D 295/22* | (2006.01) |
| *C07D 261/20* | (2006.01) |

(52) U.S. Cl. ............ 544/159; 544/160; 546/291; 546/305; 546/309; 546/332; 548/241; 560/28; 560/35; 562/440; 564/84; 564/91; 564/153; 564/164; 514/238.2; 514/346; 514/352; 514/357; 514/379; 514/510; 514/563; 514/601; 514/602; 514/604; 514/616; 514/620

(58) Field of Classification Search .......... None
See application file for complete search history.

(56) References Cited

U.S. PATENT DOCUMENTS 5,574,064 A    11/1996    Shibata et al.

FOREIGN PATENT DOCUMENTS

| EP | 1078917 | 2/2001 |
|---|---|---|
| WO | WO9822125 | 5/1998 |

OTHER PUBLICATIONS

Database CAPLUS on STN, Acc. No. 1995:763507, Shibata et al., WO 9425432 (Nov. 10, 1994) (abstract).*
Database CAPLUS on STN, Acc. No. 2001:923632, Bylund et al., WO 2001 095932 (Dec. 20, 2001) (abstract).*

* cited by examiner

*Primary Examiner*—Brian Davis
(74) *Attorney, Agent, or Firm*—Hueschen and Sage

(57) ABSTRACT

Compound of formula (I):

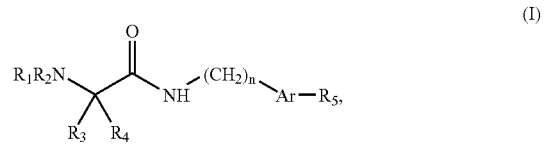

wherein:
$R_1$ represents aryl, heteroaryl or alkyl which is optionally substituted, or a group of formula $-(CO)-CR_6R_7NR_8R_9$ wherein $R_6$, $R_7$, $R_8$ and $R_9$ are as defined in the description,
$R_2$ represents hydrogen or alkyl, $R_3$ represents hydrogen or optionally substituted alkyl,
$R_4$ represents a saturated or unsaturated, 7- to 15-membered bicyclic system or optionally substituted alkyl, or $R_3$ and $R_4$, together with the carbon atom carrying them, form a saturated or unsaturated, 3- to 18-membered, mono-, bi- or tri-cyclic system optionally containing one or more hetero atoms selected from O, S and N and optionally substituted,
n represents 1 or 2,
Ar represents aryl or heteroaryl,
$R_5$ represents amino, guanidino, cyano or amidino which is optionally substituted, its optical isomers, and also addition salts thereof with a pharmaceutically acceptable acid.
Medicinal products containing the same which are useful in pathological conditions involving activated protein C.

19 Claims, No Drawings

AMINO ACID DERIVATIVES, METHOD FOR PRODUCTION THEREOF AND PHARMACEUTICAL COMPOSITIONS COMPRISING SAID DERIVATIVE

The present invention relates to new amino acid compounds, to a process for their preparation, to pharmaceutical compositions containing them and to the use thereof as inhibitors of trypsin-related serine proteases.

One of those serine proteases, activated protein C, is the key enzyme in a powerful physiological anticoagulation process, as its natural substrates, activated factor V and activated factor VIII, are potent promoters of blood coagulation (Dahlbäck B, Thrombosis Research 1995, 77, 1-43).

Direct and specific inhibition of activated protein C is an effective means of inhibiting that natural anticoagulant process and of promoting blood coagulation in haemorrhagic clinical situations and accordingly represents an extremely promising approach in the treatment of disorders involving a dysfunction of haemostasis requiring procoagulant treatment, such as von Willebrand's disease or haemophilia A or B.

Peptidomimetic compounds having inhibitory activity with respect to activated protein C have already been described in the patent specification WO98/22125.

It has been especially valuable to synthesise new serine protease inhibitors in order to increase the potency and selectivity of the compounds already described in the literature.

Moreover, in the presence of traces of tissue factor and thrombomodulin, these new compounds increase the generation of thrombin in human plasma and they are active via the oral route.

More specifically, the present invention relates to compounds of formula (I):

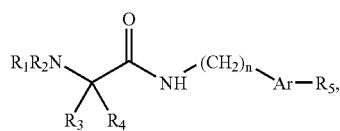

wherein:
$R_1$ represents an aryl group, a heteroaryl group or a linear or branched ($C_1$-$C_6$)alkyl group optionally substituted by one or more identical or different groups selected from aryl and heteroaryl, or $R_1$ represents a group of formula —(CO)—$CR_6R_7NR_8R_9$ wherein:
$R_6$ represents a hydrogen atom or a group selected from aryl, heteroaryl, heterocycloalkyl, ($C_3$-$C_8$)cycloalkyl and linear or branched ($C_1$-$C_6$)alkyl optionally substituted by one or more identical or different groups selected from aryl, heteroaryl, heterocycloalkyl, ($C_3$-$C_8$)cycloalkyl and carboxy,
$R_7$ represents a hydrogen atom or a linear or branched ($C_1$-$C_6$)alkyl group,
or $R_6$ and $R_7$ together form a ($C_3$-$C_8$)cycloalkyl group,
$R_8$ represents a hydrogen atom or a linear or branched ($C_1$-$C_6$)alkyl group,
and $R_9$ represents a hydrogen atom or a group $R'_9$ wherein $R'_9$ represents a group selected from:
linear or branched ($C_1$-$C_6$)alkyl optionally substituted by an aryl, carboxy, linear or branched ($C_1$-$C_6$)alkoxy-carbonyl or carbamoyl group,
aryl,
heteroaryl,
and sulphonyl substituted by a group selected from ($C_3$-$C_8$)cycloalkyl, heterocycloalkyl, aryl (optionally substituted by an aryloxy or heteroaryloxy group), and linear or branched ($C_1$-$C_6$)alkyl optionally substituted by an aryl, heteroaryl, ($C_3$-$C_8$)cycloalkyl or heterocycloalkyl group,
$R_2$ represents a hydrogen atom or a linear or branched ($C_1$-$C_6$)alkyl group,
$R_3$ represents a hydrogen atom or a linear or branched ($C_1$-$C_6$)alkyl group optionally substituted by one or more aryl groups,
$R_4$ represents a saturated or unsaturated, 7- to 15-membered bicyclic system or a linear or branched ($C_1$-$C_6$)alkyl group optionally substituted by one or more aryl groups, or $R_3$ and $R_4$, together with the carbon atom carrying them, form a saturated or unsaturated, 3- to 18-membered, mono-, bi- or tri-cyclic system optionally containing one or more hetero atoms selected from O, S and N and optionally substituted by one or more identical or different groups selected from halogen, linear or branched ($C_1$-$C_6$)alkyl, linear or branched ($C_1$-$C_6$)alkoxy, hydroxy, linear or branched ($C_1$-$C_6$)trihaloalkyl, amino (optionally substituted by one or more linear or branched ($C_1$-$C_6$)alkyl groups) and carboxy,
n represents zero, 1 or 2,
Ar represents an aryl or heteroaryl group,
$R_5$ represents a group selected from amino, guanidino, cyano and amidino optionally substituted by a hydroxy or linear or branched ($C_1$-$C_6$)alkoxy-carbonyl group, to their optical isomers, and also to addition salts thereof with a pharmaceutically acceptable acid.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

A heterocycloalkyl group is understood to mean a 3- to 8-membered, saturated monocyclic group containing one, two or three hetero atoms selected from oxygen, nitrogen and sulphur, it being understood that the heterocycle may optionally be substituted by one or more identical or different groups selected from halogen, linear or branched ($C_1$-$C_6$)alkyl, linear or branched ($C_1$-$C_6$)alkoxy, oxo, hydroxy, linear or branched ($C_1$-$C_6$)trihaloalkyl and amino (optionally substituted by one or more linear or branched ($C_1$-$C_6$) alkyl groups). Preferred heterocycloalkyl groups are morpholinyl, piperazinyl or piperidyl groups.

An aryl group is understood to mean phenyl, biphenylyl or naphthyl, each of those groups being optionally substituted by one or more identical or different groups selected from halogen, linear or branched ($C_1$-$C_6$)alkyl, linear or branched ($C_1$-$C_6$)alkoxy, hydroxy, linear or branched ($C_1$-$C_6$)trihaloalkyl, amino (optionally substituted by one or more linear or branched ($C_1$-$C_6$)alkyl groups) and carboxy.

A heteroaryl group is understood to mean a monocyclic aromatic group or a bicyclic group in which at least one of the rings is aromatic, comprising from 5 to 12 members and containing one, two or three identical or different hetero atoms selected from oxygen, nitrogen and sulphur, it being understood that the heteroaryl may optionally be substituted by one or more identical or different groups selected from halogen, linear or branched $(C_1-C_6)$alkyl, hydroxy, linear or branched $(C_1-C_6)$alkoxy, trihalomethyl and amino (optionally substituted by one or more linear or branched $(C_1-C_6)$ alkyl groups). Among the heteroaryl groups there may be mentioned, without implying any limitation, thienyl, pyridyl, furyl, pyrrolyl, imidazolyl, oxazolyl, isoxazolyl, thiazolyl, isothiazolyl, pyrimidinyl, pyrazinyl, pyridazinyl, pyrazolyl and quinolyl groups.

Preferred heteroaryl groups are pyridyl (optionally substituted), benzisoxazolyl and indazolyl groups.

An advantageous aspect of the invention relates to compounds of formula (I) wherein $R_1$ represents a group of formula —(CO)—$CHR_6NHR_9$ wherein $R_6$ represents a $(C_3-C_8)$cycloalkyl group, or linear or branched $(C_1-C_6)$alkyl optionally substituted by a $(C_3-C_8)$cycloalkyl group, and $R_9$ represents a group selected from linear or branched $(C_1-C_6)$ alkyl optionally substituted by a carboxy, linear or branched $(C_1-C_6)$alkoxycarbonyl or carbamoyl group, and linear or branched $(C_1-C_6)$alkylsulphonyl substituted by a $(C_3-C_8)$ cycloalkyl group.

Another advantageous aspect of the invention relates to compounds of formula (I) wherein $R_3$ and $R_4$, which may be the same or different, each represent a linear or branched $(C_1-C_6)$alkyl group.

Another advantageous aspect of the invention relates to compounds of formula (I) wherein $R_3$ and $R_4$ together form an optionally substituted indanyl group or a cyclopentapyridyl group.

Another advantageous aspect of the invention relates to compounds of formula (I) wherein n represents 1.

Another advantageous aspect of the invention relates to compounds of formula (I) wherein Ar represents a phenyl group and $R_5$ represents an amidino group optionally substituted by a hydroxy group.

Another advantageous aspect of the invention relates to compounds of formula (I) wherein Ar represents a pyridyl group substituted by a methyl group and $R_5$ represents an amino group.

When $R_1$ represents a group of formula —(CO)—$CHR_6NR_8R_9$ wherein $R_6$, $R_8$ and $R_9$ are as defined for formula (I), the carbon atom carrying the substituents $R_6$ and $NR_8R_9$ constitutes a centre of asymmetry, the configuration of which is preferably R.

Among the preferred compounds of the invention there may be mentioned more especially:

{[(1R)-2-({2-[({4-amidinobenzyl}-amino)-carbonyl]-indan-2-yl}-amino)-1-cyclohexyl-2-oxoethyl]-amino}acetic acid, its optical isomers, and also addition salts thereof with a pharmaceutically acceptable acid, ethyl {[(1R)-2-({2-[({4-[amino-(hydroxyimino)-methyl]-benzyl}-amino)-carbonyl]-indan-2-yl}-amino)-1-cyclohexyl-2-oxoethyl]-amino}acetate, its optical isomers, and also addition salts thereof with a pharmaceutically acceptable acid, {[(1R)-2-({2-[({4-amidinobenzyl}-amino)-carbonyl]-indan-2-yl}-amino)-1-cyclohexylmethyl-2-oxoethyl]-amino}acetic acid, its optical isomers, and also addition salts thereof with a pharmaceutically acceptable acid, {[(1R)-2-({2-[({4-amidinobenzyl}-amino)-carbonyl]-indan-2-yl}-amino)-1-isopropyl-2-oxoehtyl]-amino}acetic acid, its optical isomers, and also addition salts thereof with a pharmaceutically acceptable acid, N-(4-amidinobenzyl)-2-[((2R)-2-cyclohexyl-2-{[(cyclohexylmethyl)-sulphonyl]-amino}-ethanoyl)-amino]-2-indancarboxamide, its optical isomers, and also addition salts thereof with a pharmaceutically acceptable acid, N-(4-amidinobenzyl)-2-[((2R)-2-{[(cyclohexylmethyl)-sulphonyl]-amino}-3-methylbutanoyl)-amino]-2-indancarboxamide, its optical isomers, and also addition salts thereof with a pharmaceutically acceptable acid, N-(4-amidinobenzyl)-2-[((2R)-2-{[isobutylsulphonyl]-amino}-3-methylbutanoyl)-amino]-2-indancarboxamide, its optical isomers, and also addition salts thereof with a pharmaceutically acceptable acid, and N-(4-amidinobenzyl)-6-[((2R)-2-{[(cyclohexylmethyl)-sulphonyl]-amino}-3-methylbutanoyl)-amino]-6,7-dihydro-5H-cyclopenta[b]pyridine-6-carboxamide, its optical isomers, and also addition salts thereof with a pharmaceutically acceptable acid.

The invention relates also to a process for the preparation of compounds of formula (I), which process is characterised in that a compound of formula (II):

wherein $R_3$ and $R_4$ are as defined for formula (I) and $P_1$ represents a protecting group for the amino function, is reacted, under peptide coupling conditions, with a compound of formula (III):

wherein n and Ar are as defined for formula (I) and $R'_5$ represents a group selected from amino, guanidino and amidino optionally substituted by a hydroxy or linear or branched $(C_1-C_6)$alkoxy-carbonyl group, each of those groups being optionally substituted by a protecting group, to yield, after deprotection, the compound of formula (IV):

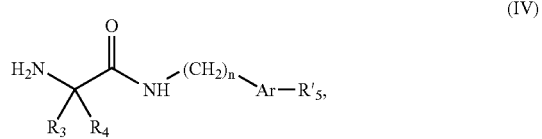

wherein $R_3$, $R_4$, n, Ar and $R'_5$ are as defined hereinbefore, which is reacted:

either, when it is desired to obtain compounds of formula (I) wherein $R_1$ represents an aryl group, a heteroaryl group or a linear or branched $(C_1-C_6)$alkyl group which is optionally substituted, with a compound of formula (V):

wherein $R_{1a}$ represents an aryl group, a heteroaryl group or a linear or branched $(C_1-C_6)$alkyl group optionally substituted by one or more groups selected from aryl and heteroaryl, and Z represents a leaving group such as, for example, a halogen atom or a tosylate, mesylate or triflate group, to yield, after optional deprotection, the compounds of formula (Ia), a particular case of the compounds of formula (I):

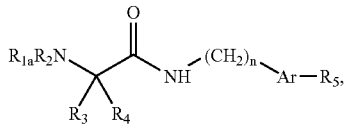
(Ia)

wherein $R_{1a}$, $R_2$, $R_3$, $R_4$, n, Ar and $R_5$ are as defined hereinbefore, or, when it is desired to obtain compounds of formula (I) wherein $R_1$ represents an optionally substituted, linear or branched ($C_2$-$C_6$)alkyl group, with a compound of formula (VI), under reductive amination conditions:

  (VI), wherein $R_{1b}$ represents a linear or branched ($C_1$-$C_5$)alkyl group optionally substituted by one or more groups selected from aryl and heteroaryl, to yield, after optional deprotection, the compounds of formula (Ib), a particular case of the compounds of formula (I):

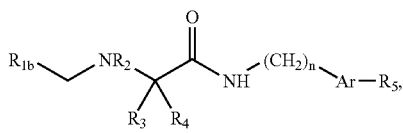
(Ib)

wherein $R_{1b}$, $R_2$, $R_3$, $R_4$, n, Ar and $R_5$ are as defined hereinbefore, or, when it is desired to obtain compounds of formula (I) wherein $R_1$ represents a group of formula —(CO)— $CR_6R_7NR_8R_9$, wherein $R_6$, $R_7$, $R_8$ and $R_9$ are as defined for formula (I), with a compound of formula (VII), under peptide coupling conditions:

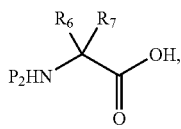
(VII)

wherein $R_6$ and $R_7$ are as defined for formula (I) and $P_2$ represents a protecting group for the amino function, to yield, after deprotection, the compound of formula (VIII):

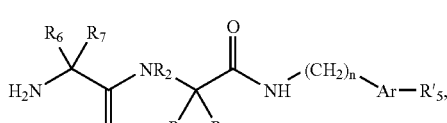
(VIII)

wherein $R_6$, $R_7$, $R_2$, $R_3$, $R_4$, n, Ar and $R'_5$ are as defined hereinbefore, which is reacted, if desired, with a compound of formula (IX):

 (IX), wherein $R'_9$ is as defined for formula (I) and Z represents a leaving group such as, for example, a halogen atom or a tosylate, mesylate or triflate group, to yield the compound of formula (X):

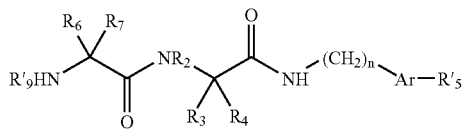
(X)

wherein $R'_9$, $R_6$, $R_7$, $R_2$, $R_3$, $R_4$, n, Ar and $R'_5$ are as defined hereinbefore, which compounds of formula (VIII) or (X) are reacted, if desired, with a compound of formula (XI):

 (XI), wherein $R'_8$ represents a linear or branched ($C_1$-$C_6$)alkyl group and Z represents a leaving group such as, for example, a halogen atom or a tosylate, mesylate or triflate group, to yield the compound of formula (XII):

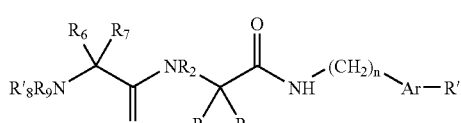
(XII)

wherein $R'_8$, $R_6$, $R_7$, $R_2$, $R_3$, $R_4$, n, Ar and $R'_5$ are as defined hereinbefore and $R_9$ is as defined for formula (I), which compounds of formula (VIII), (X) or (XII) are optionally deprotected to yield the compound of formula (Ic), a particular case of the compounds of formula (I):

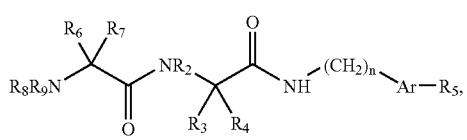
(Ic)

wherein $R_8$, $R_9$, $R_6$, $R_7$, $R_2$, $R_3$, $R_4$, n, Ar and $R_5$ are as defined hereinbefore, the compounds of formulae (Ia), (Ib) and (Ic) constituting the totality of the compounds of formula (I), which are purified, if necessary, according to a conventional purification technique, are separated, if desired, into their isomers according to a conventional separation technique and are converted, if desired, into their addition salts with a pharmaceutically acceptable acid.

Besides the fact that the compounds of the present invention are new, they possess especially valuable pharmacological properties.

They are powerful inhibitors of activated protein C, making them useful in the treatment of any pathological condition involving activated protein C and especially in the treatment of disorders involving a dysfunction of haemostasis requiring procoagulant treatment, including all haemorrhagic clinical situations such as von Willebrand's disease or haemophilia A or B.

They may also be used as antidote medicaments in antithrombotic treatments such as anticoagulant, antiplatelet and fibrinolytic treatments.

The invention relates also to pharmaceutical compositions comprising, as active ingredient, a compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Examples that follow illustrate the invention but do not limit it in any way.

The starting materials used are products that are known or that are prepared according to known operating procedures.

Preparations A to F yield synthesis intermediates that are useful in preparing compounds of the invention.

The structures of the compounds described in the Examples were determined according to the usual spectrophotometric techniques (infrared, NMR, mass spectrometry).

Preparation A: Benzyl [4-aminomethyl-phenyl]-(imino)-methyl-carbamate

The expected product is obtained according to the procedure described by G. De Nanteuil et al. (Synth. Comm. 1998, Vol. 28 N° 23, pp. 4419-4429).

Preparation B: Benzyl [4-aminomethyl-phenyl]-(hydroxyimino)-methyl-carbamate

The expected product is obtained according to the procedure described by G. De Nanteuil et al. (Synth. Comm. 1998, Vol. 28 N° 23, pp. 4419-4429).

Preparation C: 6-Amino-3-aminomethyl-2-methylpyridine

Step A: 6-Amino-3-cyano-2-methylpyridine

Copper(I) cyanide (12 mmol) is added to 10 mmol of 6-amino-3-bromo-2-methylpyridine dissolved in dimethylformamide. The mixture is refluxed for 10 hours, then cooled to 80° C. and poured into a solution of sodium cyanide (40 mmol) in water. After stirring for 1 hour at ambient temperature, the mixture is extracted with ethyl acetate. The organic phase is washed and then dried and evaporated to yield the expected product in the form of an ochre solid.

Step B: 6-Amino-3-aminomethyl-2-methylpyridine

A solution of the compound described in the Step above (10 mmol) in ethanol is placed under hydrogen overnight in the presence of Raney nickel. After filtering off the catalyst, the solvent is evaporated off to yield the expected product.

Preparation D: Methyl [4-aminomethyl-phenyl]-(imino)-methyl-carbamate

The expected product is obtained according to the procedure described by G. De Nanteuil et al. (Synth. Comm. 1998, Vol. 28 N° 23, pp. 4419-4429), starting from 4-bromomethyl-benzonitrile and methyl chloroformate.

Preparation E: Hexyl [4-aminomethyl-phenyl]-(imino)-methyl-carbamate

The expected product is obtained according to the procedure described by G. De Nanteuil et al. (Synth. Comm. 1998, Vol. 28 N° 23, pp. 4419-4429), starting from 4-bromomethyl-benzonitrile and hexyl chloroformate.

Preparation F: 4-Aminomethyl-N-hydroxybenzenecarboximidamide

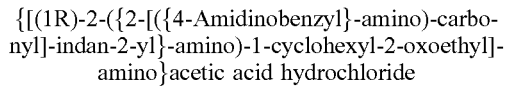

The expected product is obtained according to the procedure described by G. De Nanteuil et al. (Synth. Comm. 1998, Vol. 28 N° 23, pp. 4419-4429).

EXAMPLE 1

{[(1R)-2-({2-[({4-Amidinobenzyl}-amino)-carbonyl]-indan-2-yl}-amino)-1-cyclohexyl-2-oxoethyl]-amino}acetic acid hydrochloride Step A: Benzyl (4-{[({2-[(tert-butyloxycarbonyl)-amino]-indan-2-yl}-carbonyl)-amino]methyl}-phenyl)-(imino)-methyl-carbamate To a solution of 2-[(tert-butyloxycarbonyl)-amino]-2-indancarboxylic acid (10 mmol) and the compound described in Preparation A (10 mmol) in dimethylformamide there are added O-(1H-benzotriazol-1-yl)-N,N,N',N'-tetramethyluronium tetrafluoroborate (11 mmol) and diisopropylethylamine (11 mmol). After stirring overnight at ambient temperature, the solvent is evaporated off. The residue obtained is taken up in ethyl acetate. The organic phase is washed, dried and then evaporated. The expected product is obtained after purification of the residue by chromatography on silica gel, using a mixture of dichloromethane/ethyl acetate (1/1) as eluant.

Step B: Benzyl (4-{[({2-amino-indan-2-yl}-carbonyl)-amino]-methyl}-phenyl)-(imino)-methyl-carbamate dihydrochloride For 30 minutes, a current of HCl gas is passed, with stirring, at 0° C., into a solution of the compound described in the Step above (10 mmol) in ethyl acetate. After stirring overnight at ambient temperature, the precipitate formed is filtered off, rinsed with ethyl acetate and then dried in vacuo using a desiccator.

Step C: Benzyl {4-[({[2-({(2R)-2-[(tert-butyloxycarbonyl)-amino]-2-cyclohexyl-ethanoyl}-amino)-indan-2-yl]-carbonyl}-amino)-methyl]-phenyl}-(imino)-methylcarbamate To a solution of the compound described in the Step above (10 mmol) and (R)-N-(tert-butyloxycarbonyl)-cyclohexylglycine (10 mmol) in dimethylformamide there are added O-(1H-benzotriazol-1-yl)-N,N,N',N'-tetramethyluronium tetrafluoroborate (11 mmol), 1-hydroxybenzotriazole hydrate (11 mmol) and diisopropylethylamine (11 mmol). After stirring overnight at ambient temperature, the solvent is evaporated off. The residue obtained is taken up in ethyl acetate. The organic phase is washed, dried and then evaporated. The expected product is obtained after purification of the residue by chromatography on silica gel, using a mixture of dichloromethane/ethyl acetate (1/1) as eluant.

Step D: Benzyl {4-[({[2-({(2R)-2-amino-2-cyclohexylethanoyl}-amino)-indan-2-yl]-carbonyl}-amino)-methyl]-phenyl}-(imino)-methylcarbamate dihydrochloride For 30 minutes, a current of HCl gas is passed, with stirring, at 0° C., into a solution of the compound described in the Step above (10 mmol) in ethyl acetate. After stirring overnight at ambient temperature, the precipitate formed is filtered off, rinsed with ethyl acetate and then dried in vacuo using a desiccator.

Step E: Benzyl {[(1R)-2-({2-[({4-[{(benzyloxycarbonyl)-amino}-(imino)-methyl]-benzyl}-amino)-carbonyl]-indan-2-yl}-amino)1-cyclohexyl-2-oxoethyl]-amino}-acetate To a solution of the compound described in the Step above (10 mmol) in acetonitrile there are added potassium carbonate (30 mmol) and then benzyl 2-bromoacetate (11 mmol). After stirring overnight, the solution is filtered and evaporated; the residue is taken up in ethyl acetate, and the organic phase is washed, dried and evaporated.

Step F: {[(1R)-2-({2-[({4-Amidinobenzyl}-amino)-carbonyl]-indan-2-yl}-amino)-1-cyclohexyl-2-oxoethyl]-amino}acetic acid hydrochloride A solution of the compound described in the Step above (10 mmol) in ethanol is placed under hydrogen overnight in the presence of 10% Pd/C (0.5 g). After filtering off the catalyst, the solvent is evaporated off to yield, after conversion into a salt using hydrochloric acid, the expected product.

Elemental Microanalysis:

|  | % C | % H | % N | % Cl |
|---|---|---|---|---|
| Calculated: | 62.04 | 6.69 | 12.92 | 6.54 |
| Found: | 61.61 | 6.35 | 12.74 | 7.86 |

EXAMPLE 2

{[(1R)-2-({1-[({4-Amidinobenzyl}-amino)-carbonyl]-cyclohexyl}-amino)-1-cyclohexyl-2-oxoethyl]-amino}acetic acid hydrochloride The expected product is obtained according to the procedure described in Example 1, replacing the 2-[(tert-butyloxycarbonyl)-amino]-2-indancarboxylic acid by 1-[(tert-butyloxycarbonyl)-amino]-cyclohexanecarboxylic acid.

Elemental Microanalysis:

|  | % C | % H | % N | % Cl |
|---|---|---|---|---|
| Calculated: | 59.10 | 7.54 | 13.78 | 6.98 |
| Found: | 59.20 | 7.30 | 13.52 | 8.09 |

EXAMPLE 3

[((1R)-2-{[2-({4-Amidinobenzyl}-amino)-1,1-dimethyl-2-oxoethyl]-amino}-1-cyclohexyl-2-oxoethyl)-amino]acetic acid hydrochloride The expected product is obtained according to the procedure described in Example 1, replacing the 2-[(tert-butyloxycarbonyl)-amino]-2-indancarboxylic acid by N-(tert-butyloxycarbonyl)-2-methylalanine.

EXAMPLE 4

N-(4-Amidinobenzyl)-2-({(2R)-2-[(benzylsulphonyl)-amino]-2-cyclohexylethanoyl}-amino)-2-methypropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and phenylmethanesulphonyl chloride.

Elemental Microanalysis:

|  | % C | % H | % N | % Cl | % S |
|---|---|---|---|---|---|
| Calculated: | 57.48 | 6.79 | 12.41 | 6.28 | 5.68 |
| Found: | 57.75 | 6.97 | 12.35 | 5.94 | 5.59 |

EXAMPLE 5

N-(4-Amidinobenzyl)-1-({(2R)-2-[(benzylsulphonyl)-amino]-2-cyclohexylethanoyl}-amino)-cyclopentanecarboxamide hydrochloride The expected product is obtained according to the procedure described in Example 1, starting from 1-[(tert-butyloxycarbonyl)-amino]-cyclopentanecarboxylic acid, the compound described in Preparation A, (R)-N-(tert-butyloxycarbonyl)-cyclohexylglycine and phenylmethanesulphonyl chloride.

EXAMPLE 6

N-(4-Amidinobenzyl)-2-({(2R)-2-[([1,1'-biphenyl]4-yl-sulphonyl)-amino]-2-cyclohexylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and [1,1'-biphenyl]-4-sulphonyl chloride.

Elemental Microanalysis:

|  | % C | % H | % N | % Cl | % S |
|---|---|---|---|---|---|
| Calculated: | 61.38 | 6.44 | 11.18 | 5.66 | 5.12 |
| Found: | 60.47 | 6.51 | 11.00 | 6.00 | 4.86 |

EXAMPLE 7

N-(4-Amidinobenzyl)-2-({(2R)-2-[(phenylsulphonyl)-amino]-2-cyclohexylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and benzenesulphonyl chloride.

EXAMPLE 8

N-(4-Amidinobenzyl)-2-({(2R)-2-[(2-naphthylsulphonyl)-amino]-2-cyclohexylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and 2-naphthalenesulphonyl chloride.

Elemental Microanalysis:

|  | % C | % H | % N | % Cl | % S |
|---|---|---|---|---|---|
| Calculated: | 60.04 | 6.38 | 11.67 | 5.91 | 5.34 |
| Found: | 60.03 | 6.47 | 11.37 | 5.79 | 5.25 |

EXAMPLE 9

N-(4-Amidinobenzyl)-2-({(2R)-2-[[4-(4-pyridyloxy)-phenylsulphonyl]-amino]-2-cyclohexylethanoyl}-amino)-2-methylpropionamide dihydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and 4-(4-pyridyloxy)-benzenesulphonyl chloride.

Elemental Microanalysis:

|  | % C | % H | % N | % Cl | % S |
|---|---|---|---|---|---|
| Calculated: | 54.78 | 5.93 | 12.36 | 10.43 | 4.72 |
| Found | 55.16 | 6.02 | 12.24 | 10.37 | 4.41 |

EXAMPLE 10

N-(4-Amidinobenzyl)-2-({(2R)-2-[(benzylsulphonyl)-amino]-2-phenylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-phenylglycine and phenylmethanesulphonyl chloride.

Elemental Microanalysis:

|  | % C | % H | % N | % Cl | % S |
|---|---|---|---|---|---|
| Calculated: | 55.30 | 6.51 | 12.40 | 8.79 | 5.68 |
| Found: | 54.67 | 6.58 | 12.74 | 8.89 | 5.06 |

EXAMPLE 11

N-(4-Amidinobenzyl)-2-({(2R)-2-[[(4-pyridyl)-methyl-sulphonyl]-amino]-2-cyclohexylethanoyl}-amino)-2-methylpropionamide dihydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and (4-pyridyl)-methanesulphonyl chloride.

Elemental Microanalysis:

|  | % C | % H | % N | % Cl | % S |
|---|---|---|---|---|---|
| Calculated: | 51.91 | 6.37 | 13.97 | 11.79 | 5.33 |
| Found | 52.53 | 6.22 | 14.21 | 10.93 | 5.07 |

EXAMPLE 12

{[(1R)-2-({1-[({4-Amidinobenzyl}-amino)-carbonyl]-cyclopentyl}-amino)-1-(dicyclohexylmethyl)-2-oxoethyl]-amino}acetic acid hydrochloride The expected product is obtained according to the procedure described in Example 1, starting from 1-[(tert-butyloxycarbonyl)-amino]-cyclopentanecarboxylic acid, the compound described in Preparation A, (R)-N-(tert-butyloxycarbonyl)-dicyclohexylalanine and benzyl 2-bromoacetate.

Elemental Microanalysis:

|  | % C | % H | % N | % Cl |
|---|---|---|---|---|
| Calculated: | 61.57 | 8.07 | 11.58 | 8.21 |
| Found | 61.58 | 8.00 | 11.25 | 7.75 |

EXAMPLE 13

N-(4-Amidinobenzyl)-2-({(2R)-2-[(cyclohexylmethylsulphonyl)-amino]-2-cyclohexylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and cyclohexylmethanesulphonyl chloride.

Elemental Microanalysis:

|  | % C | % H | % N | % Cl | % S |
|---|---|---|---|---|---|
| Calculated: | 58.11 | 5.78 | 12.55 | 6.35 | 5.75 |
| Found | 58.05 | 5.84 | 12.45 | 6.34 | 5.76 |

Elemental Microanalysis:

|  | % C | % H | % N | % Cl | % S |
|---|---|---|---|---|---|
| Calculated: | 56.88 | 7.78 | 12.28 | 6.22 | 5.62 |
| Found: | 56.95 | 7.74 | 12.16 | 6.49 | 5.35 |

EXAMPLE 14

N-(4-Amidinobenzyl)-2-({(2R)-2-[(4-morpholinyl-sulphonyl)-amino]-2-cyclohexylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and 4-morpholinesulphonyl chloride.

Elemental Microanalysis:

|  | % C | % H | % N | % Cl | % S |
|---|---|---|---|---|---|
| Calculated: | 51.56 | 7.03 | 15.03 | 6.34 | 5.73 |
| Found: | 51.67 | 6.69 | 15.10 | 7.12 | 5.37 |

EXAMPLE 15

N-(4-Amidinobenzyl)-2-({(2R)-2-[[3-(4-morpholinyl)-propylsulphonyl]-amino]-2-cyclohexylethanoyl}-amino)-2-mehtylpropionamide dihydrochloride The expected product is obtained according to the procedure described in Example 1, starting from N-(tert-butyloxycarbonyl)-2-methylalanine, the compound described in Preparation A, (R)-N-(tert-butyloxycarbonyl)-cyclohexylglycine and 3-(4-morpholinyl)-propanesulphonyl chloride.

Elemental Microanalysis:

|  | % C | % H | % N | % Cl | % S |
|---|---|---|---|---|---|
| Calculated: | 50.85 | 7.29 | 13.18 | 11.12 | 4.70 |
| Found: | 50.92 | 7.07 | 13.41 | 11.56 | 4.70 |

EXAMPLE 16

N-(4-Amidinobenzyl)-2-({(2R)-2-[(benzylsulphonyl)-amino]-2-cyclohexylethanoyl}-amino)-2-indancarboxamide hydrochloride The expected product is obtained according to the procedure described in Example 1, starting from 2-[(tert-butyloxycarbonyl)-amino]-2-indancarboxylic acid, the compound described in Preparation A, (R)-N-(tert-butyloxycarbonyl)-cyclohexylglycine and phenylmethanesulphonyl chloride.

Elemental Microanalysis:

|  | % C | % H | % N | % Cl | % S |
|---|---|---|---|---|---|
| Calculated: | 62.10 | 6.32 | 10.97 | 5.55 | 5.02 |
| Found: | 62.61 | 6.36 | 10.88 | 5.61 | 4.99 |

EXAMPLE 17

N-(4-Amidinobenzyl)-1-({(2R)-2-[(benzylsulphonyl)-amino]-2-cyclohexylethanoyl}-amino)-cyclohexanecarboxamide hydrochloride The expected product is obtained according to the procedure described in Example 1, starting from 1-[(tert-butyloxycarbonyl)-amino]-cyclohexanecarboxylic acid, the compound described in Preparation A, (R)-N-(tert-butyloxycarbonyl)-cyclohexylglycine and phenylmethanesulphonyl chloride.

Elemental Microanalysis:

|  | % C | % H | % N | % Cl | % S |
|---|---|---|---|---|---|
| Calculated: | 59.64 | 7.01 | 11.59 | 5.87 | 5.31 |
| Found: | 59.38 | 7.11 | 11.40 | 6.16 | 5.07 |

EXAMPLE 18

{[(1R)-2-({1-[({4-Amidinobenzyl}-amino)-carbonyl]-cyclopentyl}-amino)-1-cyclohexyl-2-oxoethyl]-amino}-acetic acid hydrochloride The expected product is obtained according to the procedure described in Example 1, starting from 1-[(tert-butyloxycarbonyl)-amino]-cyclopentanecarboxylic acid, the compound described in Preparation A, (R)-N-(tert-butyloxycarbonyl)-cyclohexylglycine and benzyl 2-bromoacetate.

Elemental Microanalysis:

|  | % C | % H | % N | % Cl |
|---|---|---|---|---|
| Calculated: | 57.08 | 7.26 | 13.87 | 9.13 |
| Found: | 57.03 | 7.17 | 13.40 | 9.31 |

EXAMPLE 19

N-(4-Amidinobenzyl)-2-({(2R)-2-[(benzylsulphonyl)-amino]-2-benzylethanoyl}-amino)-2-methylpropionamide hydrochloride The expected product is obtained according to the procedure described in Example 1, starting from N-(tert-butyloxycarbonyl)-2-methylalanine, the compound described in Preparation A, (R)-N-(tert-butyloxycarbonyl)-phenylalanine and phenylmethanesulphonyl chloride.

Elemental Microanalysis:

|  | % C | % H | % N | % Cl | % S |
|---|---|---|---|---|---|
| Calculated: | 58.78 | 5.99 | 12.24 | 6.20 | 5.60 |
| Found: | 59.28 | 6.10 | 11.99 | 6.21 | 5.57 |

EXAMPLE 20

Ethyl {[(1R)-2-({2-[({4-[amino-(hydroxyimino)-methyl]-benzyl}-amino)-carbonyl]-indan-2-yl}-amino)-1-cyclohexyl-2-oxoethyl]-amino}-acetate The expected product is obtained according to the procedure described in Example 1, starting from 2-[(tert-butyloxycarbonyl)-amino]-2-indancarboxylic acid, the compound described in Preparation B, (R)-N-(tert-butyloxycarbonyl)-cyclohexylglycine and ethyl 2-bromoacetate.

Elemental Microanalysis:

|  | % C | % H | % N |
|---|---|---|---|
| Calculated: | 65.55 | 7.15 | 12.74 |
| Found: | 65.47 | 6.91 | 12.59 |

EXAMPLE 21

2-{[(2R)-2-Amino-2-cyclohexylethanoyl]-amino}-N-[(6-amino-2-methyl-3-pyridyl)-methyl]-2-indancarboxamide dihydrochloride Step A: 2-Amino-N-[(6-amino-2-methyl-3-pyridyl)-methyl]-2-indancarboxamide dihydrochloride
The expected product is obtained according to the procedure described in Steps A and B of Example 1, starting from 2-[(tert-butyloxycarbonyl)-amino]-2-indancarboxylic acid and the compound described in Preparation C.
Step B: 2-{[(2R)-2-Amino-2-cyclohexylethanoyl]-amino}-N-[(6-amino-2-methyl-3-pyridyl)-methyl]-2-indancarboxamide dihydrochloride
The expected product is obtained according to the procedure described in Steps C and D of Example 1, starting from the compound obtained in the Step above and (R)-N-(tert-butyloxycarbonyl)-cyclohexylglycine.

Elemental Microanalysis:

|  | % C | % H | % N | % Cl |
|---|---|---|---|---|
| Calculated: | 59.05 | 6.94 | 13.77 | 13.94 |
| Found: | 59.35 | 6.55 | 13.60 | 14.27 |

EXAMPLE 22

{[(1R)-2-({2-[({[6-Amino-2-methyl-3-pyridyl]-methyl}-amino)-carbonyl]-indan-2-yl}-amino)-1-cyclohexyl-2-oxoethyl]-amino}acetic acid dihydrochloride The expected product is obtained according to the procedure described in Example 1, starting from 2-[(tert-butyloxycarbonyl)-amino]-2-indancarboxylic acid, the compound described in Preparation C, (R)-N-(tert-butyloxycarbonyl)-cyclohexylglycine and benzyl 2-bromoacetate.

Elemental Microanalysis:

|  | % C | % H | % N | % Cl |
|---|---|---|---|---|
| Calculated: | 57.24 | 6.58 | 12.36 | 12.52 |
| Found: | 57.53 | 6.58 | 12.31 | 12.08 |

EXAMPLE 23

N-{(6-Amino-2-methyl-3-pyridyl)-methyl}-2-({(2R)-2-[(benzylsulphonyl)-amino]-2-cyclohexylethanoyl}-amino-2-indancarboxamide hydrochloride The expected product is obtained according to the procedure described in Example 1, starting from 2-[(tert-butyloxycarbonyl)-amino]-2-indancarboxylic acid, the compound described in Preparation C, (R)-N-(tert-butyloxycarbonyl)-cyclohexylglycine and phenylmethanesulphonyl chloride.

Elemental Microanalysis:

|  | % C | % H | % N | % Cl | % S |
|---|---|---|---|---|---|
| Calculated: | 61.38 | 6.44 | 11.18 | 5.66 | 5.12 |
| Found: | 61.30 | 6.54 | 10.94 | 5.74 | 4.83 |

EXAMPLE 24

[((1R)-2-{[2-({4-Amidinobenzyl}-amino)-1,1-dimethyl-2-oxoethyl]-amino}-1-phenyl-2-oxoethyl)-amino]acetic acid hydrochloride The expected product is obtained according to the procedure described in Example 1, starting from N-(tert-butyloxycarbonyl)-2-methylalanine, the compound described in Preparation A, (R)-N-(tert-butyloxycarbonyl)-phenylglycine and benzyl 2-bromoacetate.

EXAMPLE 25

[((1R)-2-{[2-({[(3-Amino-1H-indazol-6-yl)-methyl]-amino}-carbonyl)-indan-2-yl]-amino}-1-cyclohexyl-2-oxoethyl)-amino]acetic acid hydrochloride The expected product is obtained according to the procedure described in Example 1, starting from 2-[(tert-butyloxycarbonyl)-amino]-2-indancarboxylic acid, 6-(aminomethyl)-1H-indazol-3-amine (the preparation of which is described in Patent Application WO 00/26211), (R)-N-(tert-butyloxycarbonyl)-cyclohexylglycine and benzyl 2-bromoacetate.

EXAMPLE 26

[((1R)-2-{1[2-({[(3-Amino-1,2-benzisoxazol-6-yl)-methyl]-amino}-carbonyl)-indan-2-yl]-amino}-1-cycloehexyl-2-oxoethyl)-amino]acetic acid trifluoroacetate Step A: [((1R)-2-{[2-({[(3-Amino-1,2-benzisoxazol-6-yl)-methyl]-amino}-carbonyl)-indan-2-yl]-amino}-1-cyclohexyl-2-oxoethyl)-amino]acetic acid The expected product is obtained according to the procedure described in Steps A to C of Example 1, starting from 2-[(tert-butyloxycarbonyl)-amino]-2-indancarboxylic acid, 6-(aminomethyl)-1,2-benzisoxazol-3-amine (the preparation of which is described in Patent Application WO 00/26210), (R)-N-(tert-butyloxycarbonyl)-cyclohexylglycine and benzyl 2-bromoacetate.

Step B: [((1R)-2-{[2-({[(3-Amino-1,2-benzisoxazol-6-yl)-methyl]-amino}-carbonyl)-indan-2-yl]-amino}-1-cyclohexyl-2-oxoethyl)-amino]acetic acid trifluoroacetate The expected product is obtained according to the procedure described in Step D of Example 1, replacing the HCl gas by trifluoroacetic acid.

Elemental Microanalysis:

|  | % C | % H | % N | % Cl |
|---|---|---|---|---|
| Calculated: | 59.81 | 6.42 | 13.95 | 7.06 |
| Found | 59.75 | 6.35 | 13.60 | 6.76 |

EXAMPLE 27

{[(1R)-2-({2-[({4-Amidinophenyl}-amino)-carbonyl]-indan-2-yl}-amino)-1-cyclohexyl-2-oxoethyl]-amino}acetic acid hydrochloride The expected product is obtained according to the procedure described in Example 1, replacing the compound of Preparation A by benzyl (4-aminophenyl)-(imino)-methyl-carbamate.

EXAMPLE 28

{[(1R)-2-({2-[({4-Amidinobenzyl}-amino)-carbonyl]-indan-2-yl}-amino)-1-phenyl-2-oxoethyl]-amino}acetic acid dihydrochloride The expected product is obtained according to the procedure described in Example 1, replacing the (R)-N-(tert-butyloxycarbonyl)-cyclohexylglycine by (R)-N-(tert-butyloxycarbonyl)-phenylglycine.

Elemental Microanalysis:

|  | % C | % H | % N | % Cl |
|---|---|---|---|---|
| Calculated: | 58.74 | 5.46 | 12.23 | 12.39 |
| Found | 59.06 | 5.49 | 12.14 | 12.13 |

EXAMPLE 29

{([(1R)-2-({2-[({4-Amidinobenzyl}-amino)-carbonyl]-indan-2-yl}-amino)-1-benzyl-2-oxoethyl]-amino}acetic acid dihydrochloride The expected product is obtained according to the procedure described in Example 1, replacing the (R)-N-(tert-butyloxycarbonyl)-cyclohexylglycine by (R)-N-(tert-butyloxycarbonyl)-phenylalanine.

Elemental Microanalysis:

|  | % C | % H | % N | % Cl |
|---|---|---|---|---|
| Calculated: | 59.39 | 5.67 | 11.94 | 12.09 |
| Found | 59.70 | 5.65 | 11.84 | 11.68 |

EXAMPLE 30

{[(1R)-2-({2-[({4-Amidinobenzyl}-amino)-carbonyl]-indan-2-yl}-amino)-1-cyclohexylmethyl-2-oxoethyl]-amino}acetic acid dihydrochloride The expected product is obtained according to the procedure described in Example 1, replacing the (R)-N-(tert-butyloxycarbonyl)-cyclohexylglycine by (R)-N-(tert-butyloxycarbonyl)-cyclohexylalanine.

Elemental Microanalysis:

|  | % C | % H | % N | % Cl |
|---|---|---|---|---|
| Calculated: | 58.78 | 6.63 | 11.82 | 11.97 |
| Found | 59.55 | 6.55 | 11.92 | 11.92 |

EXAMPLE 31

N-[(6-Amino-2-methyl-3-pyridyl)-methyl]-2-[(2-phenethyl)-amino]-2-indancarboxamide dihydrochloride To 10 mmol of the compound described in Step A of Example 21 dissolved in 1,2-dichloroethane there are added 10 mmol of phenylacetaldehyde and then 14 mmol of sodium triacetoxyborohydride. After stirring for 4 hours, water is added and the reaction mixture is then separated and extracted with dichloromethane. The combined organic phases are dried and then filtered and evaporated. The residue thereby obtained is purified by chromatography on silica (eluant:dichloromethane/methanol 95/5) to yield, after conversion into a salt using hydrochloric acid, the expected product.

Elemental Microanalysis:

|  | % C | % H | % N | % Cl |
|---|---|---|---|---|
| Calculated: | 63.42 | 6.39 | 11.83 | 14.98 |
| Found | 63.92 | 6.33 | 11.89 | 15.36 |

EXAMPLE 32

{[(1S)-2-({2-[({4-Amidinobenzyl}-amino)-carbonyl]-indan-2-yl}-amino)-1-cyclohexyl-2-oxoethyl]-amino}acetic acid dihydrochloride The expected product is obtained according to the procedure described in Steps C to F of Example 1, starting from the compound described in Step B of Example 1 and (S)-N-(tert-butyloxycarbonyl)-cyclohexylglycine.

Elemental Microanalysis

|  | % C | % H | % N | % Cl |
|---|---|---|---|---|
| Calculated: | 58.13 | 6.45 | 12.11 | 12.26 |
| Found: | 58.46 | 6.59 | 12.02 | 11.99 |

EXAMPLE 33

N-[(6-Amino-2-methyl-3-pyridyl)-methyl]-2-[(2,2-diphenylethyl)-amino]-2-indancarboxamide hydrochloride The expected product is obtained according to the procedure described in Example 31, replacing the phenylacetaldehyde by diphenylacetaldehyde.

Elemental Microanalysis:

|  | % C | % H | % N | % Cl |
|---|---|---|---|---|
| Calculated: | 67.75 | 6.24 | 10.20 | 12.90 |
| Found: | 68.15 | 6.18 | 10.19 | 12.96 |

EXAMPLE 34

N-[(6-Amino-2-methyl-3-pyridyl)-methyl]-2-[(3-phenylpropyl)-amino]-2-indancarboxamide hydrochloride The expected product is obtained according to the procedure described in Example 31, replacing the phenylacetaldehyde by 3-phenylpropanal.

Elemental Microanalysis:

|  | % C | % H | % N | % Cl |
|---|---|---|---|---|
| Calculated: | 64.06 | 6.62 | 11.49 | 14.55 |
| Found: | 64.74 | 6.51 | 11.59 | 14.68 |

EXAMPLE 35

N-(4-Amidinobenzyl)-2-[(2,2-diphenylethyl)-amino]-2-indancarboxamide hydrochloride Step A: Benzyl (4-{[({2-[(2,2-diphenylethyl)-amino]-indan-2-yl}-carbonyl)-amino]-methyl}-phenyl)-(imino)-methylcarbamate hydrochloride The expected product is obtained according to the procedure described in Example 31, starting from the compound obtained in Step B of Example 1 and diphenylacetaldehyde.

Step B: N-(4-Amidinobenzyl)-2-[(2,2-diphenylethyl)-amino]-2-indancarboxamide hydrochloride The expected product is obtained according to the procedure described in Step F of Example 1, starting from the compound obtained in the Step above.

Elemental Microanalysis:

|  | % C | % H | % N | % Cl |
|---|---|---|---|---|
| Calculated: | 73.20 | 6.33 | 10.67 | 6.75 |
| Found: | 72.55 | 5.96 | 10.15 | 7.42 |

EXAMPLE 36

Ethyl ({(1R)-1-cyclohexyl-2-[(2-{[(4-{imino-[(methoxycarbonyl)-amino]-methyl}-benzyl)-amino]-carbonyl}-indan-2-yl)-amino]-2-oxoethyl}-amino)-acetate The expected product is obtained according to the procedure described in Steps A to E of Example 1, replacing, in Step A, Preparation A by Preparation D and, in Step E, the benzyl 2-bromoacetate by ethyl 2-bromoacetate.

Elemental Microanalysis

|  | % C | % H | % N |
|---|---|---|---|
| Calculated: | 64.96 | 6.98 | 11.84 |
| Found: | 64.29 | 6.91 | 11.45 |

EXAMPLE 37

Ethyl ({(1R)-1-cyclohexyl-2-[(2-{[(4-{imino-[({hexyloxy}-carbonyl)-amino]-methyl}-benzyl)-amino]-carbonyl}-indan-2-yl)-amino]-2-oxoethyl}-amino)-acetate The expected product is obtained according to the procedure described in Steps A to E of Example 1, replacing, in Step A, Preparation A by Preparation E and, in Step E, the benzyl 2-bromoacetate by ethyl 2-bromoacetate.

Elemental Microanalysis:

|  | % C | % H | % N |
|---|---|---|---|
| Calculated: | 67.15 | 7.77 | 10.58 |
| Found: | 67.21 | 7.85 | 10.57 |

EXAMPLE 38

N-(4-Amidinobenzyl)-2-({(2R)-2-[(2-amino-2-oxoethyl)-amino]-2-cyclohexylethanoyl}-amino)-2-indancarboxamide hydrochloride The expected product is obtained according to the procedure of Example 1, replacing the benzyl 2-bromoacetate in Step E by 2-bromoacetamide.

Elemental Microanalysis:

|  | % C | % H | % N | % Cl |
|---|---|---|---|---|
| Calculated: | 62.15 | 6.89 | 15.53 | 6.55 |
| Found: | 62.77 | 6.70 | 15.33 | 6.75 |

EXAMPLE 39A

{[(1R)-2-({2-[({4-Amidinobenzyl}-amino)-carbonyl]-indan-2-yl}-amino)-1-isopropyl-2-oxoethyl]-amino}acetic acid hydrochloride The expected product is obtained according to the procedure of Example 1, replacing the (R)-N-(tert-butyloxycarbonyl)-cyclohexylglycine in Step C by (R)-N-(tert-butyloxycarbonyl)-valine.

Elemental Microanalysis:

|  | % C | % H | % N | % Cl |
|---|---|---|---|---|
| Calculated: | 59.81 | 6.42 | 13.95 | 7.06 |
| Found: | 59.75 | 6.35 | 13.60 | 6.76 |

EXAMPLE 39B

{[(1R)-2-({2-[({4-Amidinobenzyl}-amino)-carbonyl]-indan-2-yl}-amino)-1-isopropyl-2-oxoethyl]-amino}acetic acid dihydrochloride Elemental Microanalysis:

|  | % C | % H | % N | % Cl |
|---|---|---|---|---|
| Calculated: | 55.76 | 6.18 | 13.01 | 13.17 |
| Found: | 55.62 | 6.27 | 12.75 | 13.45 |

EXAMPLE 40

N-(4-Amidinobenzyl)-2-[((2R)-2-cyclohexyl-2-{[(cyclohexylmethyl)-sulphonyl]-amino}-ethanoyl)-amino]-2-indancarboxamide hydrochloride The expected product is obtained according to the procedure described in Example 1, starting from 2-[(tert-butyloxycarbonyl)-amino]-2-indancarboxylic acid, the compound described in Preparation A, (R)-N-(tert-butyloxycarbonyl)-cyclohexylglycine and cyclohexylmethanesulphonyl chloride.

Elemental Microanalysis:

|  | % C | % H | % N | % Cl | % S |
|---|---|---|---|---|---|
| Calculated: | 61.52 | 7.20 | 10.87 | 5.50 | 4.98 |
| Found: | 61.22 | 7.22 | 10.67 | 5.49 | 4.91 |

EXAMPLE 41

N-(4-Amidinobenzyl)-2-[((2R)-2-cyclohexyl-2-{[(cyclohexylmethyl)-sulphonyl]-amino}-ethanoyl)-amino]-2,3-dihydro-1H-cyclopenta[b]-naphthalene-2-carboxamide hydrochloride The expected product is obtained according to the procedure described in Example 1, starting from 2-[(tert-butyloxycarbonyl)-amino]-2,3-dihydro-1H-cyclopenta[b]-naphthalene-2-carboxylic acid, the compound described in Preparation A, (R)-N-(tert-butyloxycarbonyl)-cyclohexylglycine and cyclohexylmethanesulphonyl chloride.

EXAMPLE 42

N-(4-Amidinobenzyl)-2-[((2R)-2-cyclohexyl-2-{[(cyclohexylmethyl)-sulphonyl]-amino}-ethanoyl)-amino]-2,3-dihydro-1H-cyclopenta[a]-naphthalene-2-carboxamide hydrochloride The expected product is obtained according to the procedure described in Example 1, starting from 2-[(tert-butyloxycarbonyl)-amino]-2,3-dihydro-1H-cyclopenta[a]-naphthalene-2-carboxylic acid, the compound described in Preparation A, (R)-N-(tert-butyloxycarbonyl)-cyclohexylglycine and cyclohexylmethanesulphonyl chloride.

EXAMPLE 43

N-(4-Amidinobenzyl)-2-[((2R)-2-{[(cyclohexylmethyl)-sulphonyl]-amino}-3-methylbutanoyl)-amino]-2,3-dihydro-1H-cyclopenta[a]-naphthalene-2-carboxamide hydrochloride The expected product is obtained according to the procedure described in Example 1, starting from 2-[(tert-butyloxycarbonyl)-amino]-2,3-dihydro-1H-cyclopenta[a]-naphthalene-2-carboxylic acid, the compound described in Preparation A, (R)-N-(tert-butyloxycarbonyl)-valine and cyclohexylmethanesulphonyl chloride.

Elemental Microanalysis:

|  | % C | % H | % N | % Cl | % S |
|---|---|---|---|---|---|
| Calculated: | 62.42 | 6.78 | 10.70 | 4.90 | 5.42 |
| Found: | 62.95 | 7.02 | 10.65 | 4.71 | 5.39 |

EXAMPLE 44

N-(4-Amidinobenzyl)-2-[((2R)-2-{[(cyclohexylmethyl)-sulphonyl]-amino}-3-methylbutanoyl)-amino]-2,3-dihydro-1H-cyclopenta[b]-naphthalene-2-carboxamide hydrochloride The expected product is obtained according to the procedure described in Example 1, starting from 2-[(tert-butyloxycarbonyl)-amino]-2,3-dihydro-1H-cyclopenta[b]-naphthalene-2-carboxylic acid, the compound described in Preparation A, (R)-N-(tert-butyloxycarbonyl)-valine and cyclohexylmethanesulphonyl chloride.

EXAMPLE 45

{[(1R)-2-({2-[({4-Amidinobenzyl}-amino)-carbonyl]-2,3-dihydro-1H-cyclopenta[b]naphth-2-yl}-amino)-1-cylcohexyl-2-oxoethyl]-amino}-acetic acid hydrochloride The expected product is obtained according to the procedure described in Example 1, replacing the 2-[(tert-butyloxycarbonyl)-amino]-2-indancarboxylic acid in Step A by 2-[(tert-butyloxycarbonyl)-amino]-2,3-dihydro-1H-cyclopenta[b]naphthalene-2-carboxylic acid.

EXAMPLE 46

{[(1R)-2-({2-[({4-Amidinobenzyl}-amino)-carbonyl]-2,3-dihydro-1H-cyclopenta[a]naphth-2-yl}-amino)-1-cyclohexyl-2-oxoethyl]-amino}-acetic acid hydrochloride The expected product is obtained according to the procedure described in Example 1, replacing the 2-[(tert-butyloxycarbonyl)-amino]-2-indancarboxylic acid in Step A by 2-[(tert-butyloxycarbonyl)-amino]-2,3-dihydro-1H-cyclopenta[a]naphthalene-2-carboxylic acid.

EXAMPLE 47

({(1R)-1-[({2-[({4-Amidinobenzyl}-amino)-carbonyl]-2,3-dihydro-1H-cyclopenta[a]naphth-2-yl}-amino)-carbonyl]-2-methylpropyl}-amino)acetic acid hydrochloride The expected product is obtained according to the procedure described in Example 1, replacing, in Step A, the 2-[(tert-butyloxycarbonyl)-amino]-2-indancarboxylic acid by 2-[(tert-butyloxycarbonyl)-amino]-2,3-dihydro-1H-cyclopenta[a]naphthalene-2-carboxylic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 63.09 | 6.21 | 12.69 | 6.42 |
| Found: | 63.46 | 6.08 | 12.60 | 6.57 |

EXAMPLE 48

({(1R)-1-[({2-[({4-Amidinobenzyl}-amino)-carbonyl]-2,3-dihydro-1H-cyclopenta[b]naphth-2-yl}-amino)-carbonyl]-2-methylpropyl}-amino)-acetic acid hydrochloride The expected product is obtained according to the procedure described in Example 1, replacing, in Step A, the 2-[(tert-butyloxycarbonyl)-amino]-2-indancarboxylic acid by 2-[(tert-butyloxycarbonyl)-amino]-2,3-dihydro-1H-cyclopenta[b]naphthalene-2-carboxylic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 63.09 | 6.21 | 12.69 | 6.42 |
| Found: | 63.17 | 5.91 | 12.39 | 6.49 |

EXAMPLE 49

N-(4-Amidinobenzyl)-2-[((2R)-2-{[(cyclohexylmethyl)-sulphonyl]-amino}-3-methylbutanoyl)-amino]-2-indancarboxamide hydrochloride The expected product is obtained according to the procedure described in Example 1, starting from 2-[(tert-butyloxycarbonyl)-amino]-2-indancarboxylic acid, the compound described in Preparation A, (R)-N-(tert-butyloxycarbonyl)-valine and cyclohexylmethanesulphonyl chloride.

Elemental Microanalysis:

|  | % C | % H | % N | % S | % Cl |
|---|---|---|---|---|---|
| Calculated: | 59.64 | 7.01 | 11.59 | 5.31 | 5.87 |
| Found: | 59.75 | 7.07 | 11.43 | 5.22 | 5.92 |

EXAMPLE 50

N-(4-Amidinobenzyl)-2-[((2R)-2-{[(cyclohexylmethyl)-sulphonyl]-amino}-3-methylbutanoyl)-amino]-2,3-dihydro-1H-phenalene-2-carboxamide hydrochloride The expected product is obtained according to the procedure described in Example 1, starting from 2-[(tert-butyloxycarbonyl)-amino]-2,3-dihydro-1H-phenalene-2-carboxylic acid, the compound described in Preparation A, (R)-N-(tert-butyloxycarbonyl)-valine and cyclohexylmethanesulphonyl chloride.

Elemental Microanalysis:

|  | % C | % H | % N | % S | % Cl |
|---|---|---|---|---|---|
| Calculated: | 62.42 | 6.78 | 10.70 | 4.90 | 5.42 |
| Found: | 62.79 | 7.58 | 10.63 | 4.49 | 5.31 |

EXAMPLE 51

({(1R)-1-[({2-[({4-Amidinobenzyl}-amino)-carbonyl]-2,3-dihydro-1H-phenalen-2-yl}-amino)-carbonyl]-2-methylpropyl}-amino)-acetic acid dihydrochloride The expected product is obtained according to the procedure described in Example 1, replacing, in Step A, the 2-[(tert-butyloxycarbonyl)-amino]-2-indancarboxylic acid by 2-[(tert-butyloxycarbonyl)-amino]-2,3-dihydro-1H-phenalene-2-carboxylic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 59.18 | 5.99 | 11.90 | 12.05 |
| Found: | 59.56 | 5.59 | 11.85 | 11.25 |

EXAMPLE 52

N-(4-Amidinobenzyl)-2-[((2R)-2-{[isobutylsulphonyl]-amino}-3-methylbutanoyl)-amino]-2-indancarboxamide hydrochloride The expected product is obtained according to the procedure described in Example 1, starting from 2-[(tert-butyloxycarbonyl)-amino]-2-indancarboxylic acid, the compound described in Preparation A, (R)-N-(tert-butyloxycarbonyl)-valine and isobutanesulphonyl chloride.

Elemental Microanalysis:

|  | % C | % H | % N | % S | % Cl |
|---|---|---|---|---|---|
| Calculated: | 57.48 | 6.79 | 12.41 | 5.68 | 6.28 |
| Found: | 57.77 | 6.93 | 12.28 | 5.41 | 6.38 |

EXAMPLE 53

({(1R)-1-[({6-[({4-Amidinobenzyl}-amino)-carbonyl]-6,7-dihydro-5H-dibenzo[a,c]cyclohepten-6-yl}-amino)-carbonyl]-2-methylpropyl}-amino)-acetic acid dihydrochloride The expected product is obtained according to the procedure described in Example 1, replacing, in Step A, the 2-[(tert-butyloxycarbonyl)-amino]-2-indancarboxylic acid by 6-[(tert-butyloxycarbonyl)-amino]-6,7-dihydro-5H-dibenzo[a,c]cycloheptene-6-carboxylic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 60.59 | 6.07 | 11.40 | 11.54 |
| Found: | 61.11 | 6.11 | 11.34 | 11.68 |

EXAMPLE 54

N-(4-Cyanobenzyl)-2-[((2R)-2-{[(cyclohexylmethyl)-sulphonyl]-amino}-3-methylbutanoyl)-amino]-2-indancarboxamide The expected product is obtained according to the procedure described in Steps A to E of Example 1, replacing, in Step A, the compound of Preparation A by 4-(aminomethyl) benzonitrile and, in Step E, the benzyl 2-bromoacetate by cyclohexylmethanesulphonyl chloride.

Elemental Microanalysis:

|  | % C | % H | % N | % S |
|---|---|---|---|---|
| Calculated: | 65.43 | 6.95 | 10.17 | 5.82 |
| Found: | 65.28 | 6.93 | 10.17 | 5.73 |

EXAMPLE 55

N-{4-[(Hydroxyamino)-(imino)-methyl]-benzyl}-2-[((2R)-2-{[(cyclohexylmethyl)-sulphonyl]-amino}-3-methylbutanoyl)-amino]-2-indancarboxamide The expected product is obtained according to the procedure described in Steps A to E of Example 1, replacing, in Step A, the compound of Preparation A by the compound of Preparation F and, in Step E, the benzyl 2-bromoacetate by cyclohexylmethanesulphonyl chloride.

Elemental Microanalysis:

|  | % C | % H | % N | % S |
|---|---|---|---|---|
| Calculated: | 61.73 | 7.08 | 12.00 | 5.49 |
| Found: | 61.52 | 7.06 | 11.99 | 5.16 |

EXAMPLE 56

{[2-({2-[({4-Amidinobenzyl}-amino)-carbonyl]-indan-2-yl}-amino)-1,1-dimethyl-2-oxoethyl]-amino}acetic acid dihydrochloride The expected product is obtained according to the procedure described in Example 1, replacing the (R)-N-(tert-butyloxycarbonyl)-cyclohexylglycine in Step C by N-(tert-butyloxycarbonyl)-2-methylalanine.

Elemental Microanalysis:

|  | % C | % H | % N | % Cl |
|---|---|---|---|---|
| Calculated: | 54.97 | 5.96 | 13.35 | 13.52 |
| Found: | 54.97 | 5.84 | 13.13 | 12.69 |

EXAMPLE 57

({1-[({2-[({4-Amidinobenzyl}-amino)-carbonyl]-indan-2-yl}-amino)-carbonyl-cyclopentyl}-amino)-acetic acid dihydrochloride The expected product is obtained according to the procedure described in Example 1, replacing the (R)-N-(tert-butyloxycarbonyl)-cyclohexylglycine in Step C by 1-[(tert-butyloxycarbonyl)-amino]-cyclopentanecarboxylic acid.

Elemental Microanalysis:

|  | % C | % H | % N | % Cl |
|---|---|---|---|---|
| Calculated: | 56.73 | 6.04 | 12.72 | 12.88 |
| Found: | 56.57 | 5.92 | 12.61 | 12.23 |

EXAMPLE 58

({(1R)-1-[({2-[({4-Amidinobenzyl}-amino)-carbonyl]-indan-2-yl}-amino)-carbonyl]-propyl}-amino)-acetic acid dihydrochloride The expected product is obtained according to the procedure described in Example 1, replacing the (R)-N-(tert-butyloxycarbonyl)-cyclohexylglycine in Step C by (2R)-2-[(tert-butyloxycarbonyl)-amino]-butanoic acid.

Elemental Microanalysis:

|  | % C | % H | % N | % Cl |
|---|---|---|---|---|
| Calculated: | 54.97 | 5.96 | 13.35 | 13.52 |
| Found: | 54.68 | 5.85 | 13.14 | 12.87 |

EXAMPLE 59

({(1R,2R)-1-[({2-[({4-Amidinobenzyl}-amino)-carbonyl]-indan-2-yl}-amino)-carbonyl]-2-methyl-butyl}-amino)-acetic acid dihydrochloride The expected product is obtained according to the procedure described in Example 1, replacing the (R)-N-(tert-butyloxycarbonyl)-cyclohexylglycine in Step C by (2R,3R)-N-(tert-butyloxycarbonyl)-isoleucine.

Elemental Microanalysis:

|  | % C | % H | % N | % Cl |
|---|---|---|---|---|
| Calculated: | 56.52 | 6.39 | 12.68 | 12.83 |
| Found: | 57.26 | 6.43 | 12.69 | 12.61 |

EXAMPLE 60

({(1R)-1-[({2-[({4-Amidinobenzyl}-amino)-carbonyl]-indan-2-yl}-amino)-carbonyl]-2,2-dimethylpropyl}-amino)-acetic acid dihydrochloride The expected product is obtained according to the procedure described in Example 1, replacing the (R)-N-(tert-butyloxycarbonyl)-cyclohexylglycine in step C by (2R)-2-[(tert-butyloxycarbonyl)-amino]-3,3-dimethylbutanoic acid.

Elemental Microanalysis:

|  | % C | % H | % N | % Cl |
|---|---|---|---|---|
| Calculated: | 56.52 | 6.39 | 12.68 | 12.83 |
| Found: | 56.98 | 6.36 | 12.61 | 12.34 |

EXAMPLE 61

Diastereoisomer 1 of ({(1R)-1-[({6-[({4-amidinobenzyl}-amino)-carbonyl]-6,7-dihydro-5H-cyclopenta[b]pyridin-6-yl}-amino)-carbonyl]-2-methyl-propyl}-amino)-acetic acid trihydrochloride Step A : Diastereoisomer 1 of benzyl ({(1R)-1-[({6-[({4-[{[(benzyloxy)-carbonyl]-amino}-(imino)-methyl]-benzyl}-amino)-carbonyl]-6,7-dihydro-5H-cyclopenta[b]pyridin-6-yl}-amino)-carbonyl]-2-methylpropyl}-amino)-acetate The expected product is obtained according to the procedure described in Steps A to E of Example 1, replacing, in Step A, the 2-[(tert-butyloxycarbonyl)-amino]-2-indancarboxylic acid by 6-[(tert-butyloxycarbonyl)-amino]-6,7-dihydro-5H-cyclopenta[b]pyridine-6-carboxylic acid and, in Step C, the (R)-N-(tert-butyloxycarbonyl)-cyclohexylglycine by (R)-N-(tert-butyloxycarbonyl)-valine, and then separating the mixture of diastereoisomers thereby obtained by chromatography on silica.

The expected product is the first of the diastereoisomers separated in that manner.

Step B: Diastereoisomer 1 of ({(1R)-1-[({6-[({4-amidinobenzyl}-amino)-carbonyl]-6,7-dihydro-5H-cyclopenta[b]pyridin-6-yl}-amino)-carbonyl]-2-methyl-propyl}-amino)-acetic acid trihydrochloride The expected product is obtained according to the procedure described in Step F of Example 1, starting from the compound obtained in the Step above.

Elemental Microanalysis:

|  | % C | % H | % N | % Cl |
|---|---|---|---|---|
| Calculated: | 50.05 | 5.78 | 14.59 | 18.47 |
| Found: | 50.39 | 5.71 | 14.54 | 18.37 |

EXAMPLE 62

Diastereoisomer 2 of ({(1R)-1-[({6-[({4-amidinobenzyl}-amino)-carbonyl]-6,7-dihydro-5H-cyclopenta[b]pyridin-6-yl}-amino)-carbonyl]-2-methylpropyl}amino)-acetic acid trihydrochloride Step A: Diastereoisomer 2 of benzyl ({(1R)-1-[({6-[({4-[{[(benzyloxy)-carbonyl]-amino}-(imino)-methyl]-benzyl}-amino)-carbonyl]-6,7-dihydro-5H-cyclopenta[b]pyridin-6-yl}-amino)-carbonyl]-2-methylpropyl}-amino)-acetate The expected product is the second of the diastereoisomers separated in Step A of Example 61.

Step B: Diastereoisomer 2 of ({(1R)-1-[({6-[({4-amidinobenzyl}-amino)carbonyl]-6,7-dihydro-5H-cyclopenta[b]pyridin-6-yl}-amino)-carbonyl]-2-methyl-propyl}-amino)-acetic acid trihydrochloride The expected product is obtained according to the procedure described in Step F of Example 1, starting from the compound obtained in the Step above.

Elemental Microanalysis:

|  | % C | % H | % N | % Cl |
|---|---|---|---|---|
| Calculated: | 50.05 | 5.78 | 14.59 | 18.47 |
| Found: | 50.14 | 5.56 | 14.45 | 19.00 |

EXAMPLE 63

Hexyl (4-{[({2-[((2R)-2-{[(cyclohexylmethyl)-sulphonyl]-amino}-3-methylbutanoyl)-amino]-indan-2-yl}-carbonyl)-amino]-methyl}-phenyl)-(imino)-methylcarbamate The expected product is obtained according to the procedure described in Steps A to E of Example 1, starting from 2-[(tert-butyloxycarbonyl)-amino]-2-indancarboxylic acid, the compound described in Preparation E, (R)-N-(tert-butyloxycarbonyl)-valine and cyclohexylmethanesulphonyl chloride.

Elemental Microanalysis:

|  | % C | % H | % N | % S |
|---|---|---|---|---|
| Calculated: | 63.86 | 7.68 | 10.06 | 4.61 |
| Found: | 64.10 | 7.93 | 9.89 | 4.30 |

EXAMPLE 64

N-(4-Amidinobenzyl)-6-[((2R)-2-{[(cyclohexylmethyl)-sulphonyl]-amino}-3-methylbutanoyl)-amino]-6,7-dihydro-5H-cyclopenta[b]-pyridine-6-carboxamide dihydrochloride The expected product is obtained according to the procedure described in Example 1, starting from 6-[(tert-butyloxycarbonyl)-amino]-6,7-dihydro-5H-cyclopenta[b]pyridine-6-carboxylic acid, the compound described in Preparation A, (R)-N-(tert-butyloxycarbonyl)-valine and cyclohexylmethanesulphonyl chloride.

Elemental Microanalysis:

|  | % C | % H | % N | % S | % Cl |
|---|---|---|---|---|---|
| Calculated: | 54.28 | 6.60 | 13.10 | 5.00 | 11.05 |
| Found: | 54.57 | 6.57 | 13.05 | 4.99 | 10.85 |

EXAMPLE 65

({(1R)-1-[({6-[({4-Amidinobenzyl}-amino)carbonyl]-6,7-dihydro-5H-cyclopenta[c]pyridin-6-yl}-amino)-carbonyl]-2-methylpropyl}-amino)-acetic acid trihydrochloride The expected product is obtained according to the procedure described in Example 1, replacing, in Step A, the 2-[(tert-butyloxycarbonyl)-amino]-2-indancarboxylic acid by 6-[(tert-butyloxycarbonyl)-amino]-6,7-dihydro-5H-cyclopenta[c]pyridine-6-carboxylic acid and, in Step C, the (R)-N-(tert-butyloxycarbonyl)-cyclohexylglycine by (R)-N-(tert-butyloxycarbonyl)-valine.

EXAMPLE 66

N-(4-Amidinobenzyl)-2-{[(2R)-2-(isobutylamino)-3-methylbutanoyl]-amino}-2-indancarboxamide dihydrochloride The expected product is obtained according to the procedure described in Example 1, starting from 2-[(tert-butyloxycarbonyl)-amino]-2-indancarboxylic acid, the compound described in Preparation A, N-(tert-butyloxycarbonyl)-glycine and isobutyl chloride.

Elemental Microanalysis:

|  | % C | % H | % N | % Cl |
|---|---|---|---|---|
| Calculated: | 58.30 | 6.73 | 14.16 | 14.34 |
| Found: | 57.97 | 6.86 | 14.19 | 14.92 |

EXAMPLE 67

N-[(6-Amino-2-methyl-3-pyridyl)-methyl]-2-{[(2R)-2-(isobutylamino)-3-methylbutanoyl]-amino}-2-indancarboxamide dihydrochloride The expected product is obtained in the form of the base according to the procedure described in Steps C to E of Example 1, starting from the compound obtained in Step A of Example 21, N-(tert-butyloxycarbonyl)-glycine and isobutyl chloride, and is then converted into a salt using hydrochloric acid.

Elemental Microanalysis:

|  | % C | % H | % N | % Cl |
|---|---|---|---|---|
| Calculated: | 57.26 | 6.89 | 14.52 | 14.70 |
| Found: | 57.17 | 7.02 | 14.49 | 14.95 |

EXAMPLE 68

{[2-({2-[({4-Amidinobenzyl}-amino)-carbonyl]-indan-2-yl}-amino)-2-oxoethyl]-amino}acetic acid dihydrochloride The expected product is obtained according to the procedure described in Example 1, replacing the (R)-N-(tert-butyloxycarbonyl)-cyclohexylglycine in Step C by N-(tert-butyloxycarbonyl)-glycine.

Elemental Microanalysis:

|  | % C | % H | % N | % Cl |
|---|---|---|---|---|
| Calculated: | 53.23 | 5.48 | 14.11 | 14.28 |
| Found: | 53.40 | 5.56 | 14.00 | 14.32 |

EXAMPLE 69

{[(1R)-2-({2-[({4-Amidinobenzyl}-amino)-carbonyl]-5,6-dimethoxyindan-2-yl}-amino)-1-isopropyl-2-oxoethyl]-amino}-acetic acid hydrochloride The expected product is obtained according to the procedure of Example 1, replacing, in Step A, the 2-[(tert-butyloxycarbonyl)-amino]-2-indancarboxylic acid by 2-[(tert-butyloxycarbonyl)-amino]-5,6-dimethoxy-2-indancarboxylic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 57.70 | 6.46 | 12.46 | 6.31 |
| Found: | 58.06 | 6.32 | 12.50 | 6.78 |

EXAMPLE 70

({(1R)-1-[({2-[({4-Amidinobenzyl}-amino)-carbonyl]-indan-2-yl}-amino)-carbonyl]-3-methylbutyl}-amino)-acetic acid hydrochloride The expected product is obtained according to the procedure described in Example 1, replacing the (R)-N-(tert-butyloxycarbonyl)-cyclohexylglycine in Step C by (R)-N-(tert-butyloxycarbonyl)-leucine.

Elemental Microanalysis:

|  | % C | % H | % N | % Cl |
|---|---|---|---|---|
| Calculated: | 60.52 | 6.64 | 13.57 | 6.87 |
| Found: | 60.39 | 6.53 | 13.40 | 7.56 |

EXAMPLE 71

{[(1R)-2-({2-[({4-Amidinobenzyl}-amino)-carbonyl]-indan-2-yl}-amino)-1-methyl-2-oxoethyl]-amino}acetic acid dihydrochloride The expected product is obtained according to the procedure described in Example 1, replacing the (R)-N-(tert-butyloxycarbonyl)-cyclohexylglycine in Step C by (R)-N-(tert-butyloxycarbonyl)-alanine.

Elemental Microanalysis:

|  | % C | % H | % N | % Cl |
|---|---|---|---|---|
| Calculated: | 54.12 | 5.73 | 13.72 | 13.89 |
| Found: | 54.34 | 5.87 | 13.53 | 14.35 |

EXAMPLE 72

N-(4-Amidinobenzyl)-2-[((2R)-2-{[isobutylsulphonyl]-amino}-3-methylbutanoyl)-amino]-5,6-dimethoxy-2-indancarboxamide hydrochloride The expected product is obtained according to the procedure described in Example 1, starting from 2-[(tert-butyloxycarbonyl)-amino]-5,6-dimethoxy-2-indancarboxylic acid, the compound described in Preparation A, (R)-N-(tert-butyloxycarbonyl)-valine and isobutanesulphonyl chloride.

Elemental Microanalysis:

|  | % C | % H | % N | % S | % Cl |
|---|---|---|---|---|---|
| Calculated: | 55.80 | 6.78 | 11.22 | 5.14 | 5.68 |
| Found: | 55.58 | 6.94 | 11.21 | 4.90 | 6.01 |

EXAMPLE 73

{[(1R)-1-({[(1S)-2-({4-Amidinobenzyl}-amino)-1-benzyl-2-oxoethyl]-amino}-carbonyl)-2-methylpropyl]amino}-acetic acid dihydrochloride The expected product is obtained according to the procedure of Example 1, replacing, in Step A, the 2-[(tert-butyloxycarbonyl)-amino]-2-indancarboxylic acid by (S)-N-(tert-butyloxycarbonyl)-phenylalanine and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 54.75 | 6.32 | 13.30 | 13.47 |
| Found: | 54.90 | 6.40 | 13.27 | 13.08 |

EXAMPLE 74

({(1R)-1-[({(1S)-2-[{4-Amidinobenzyl}-amino)-1-benzhydryl-2-oxoethyl]-amino}-carbonyl)-2-methylpropyl]amino}-acetic acid dihydrochloride The expected product is obtained according to the procedure of Example 1, replacing, in Step A, the 2-[(tert-butyloxycarbonyl)-amino]-2-indancarboxylic acid by (2S)-2-[(tert-butyloxycarbonyl)-amino]-3,3-diphenylpropanoic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 59.80 | 6.19 | 11.62 | 11.77 |
| Found: | 60.35 | 6.15 | 11.88 | 11.62 |

EXAMPLE 75

({(1R)-1-[({(1S)-2-[{4-Amidinobenzyl}-amino)-1-(2,3-dihydro-1H-inden-2-yl)-2-oxoethyl]-amino}-carbonyl)-2-methylpropyl]-amino}-acetic acid dihydrochloride The expected product is obtained according to the procedure of Example 1, replacing, in Step A, the 2-[(tert-butyloxycarbonyl)-amino]-2-indancarboxylic acid by (2S)-2-[(tert-butyloxycarbonyl)-amino]-(2,3-dihydro-1H-inden-2-yl)ethanoic acid and, in Step C, the (R)-N-(tert-butyloxycarbonyl)-cyclohexylglycine by (R)-N-(tert-butyloxycarbonyl)-valine.

Elemental Microanalysis:

|  | % C | % H | % N | % Cl |
|---|---|---|---|---|
| Calculated: | 56.52 | 6.39 | 12.68 | 12.83 |
| Found: | 56.63 | 6.57 | 12.80 | 12.62 |

PHARMACOLOGICAL STUDY OF COMPOUNDS OF THE INVENTION

EXAMPLE 76

Inhibition of Activated Protein C and of Coagulation and Fibrinolysis Serine Proteases In order to assess in vitro the inhibitory activity of products of the invention on purified human activated protein C (Diagnostica Stago), the chromogenic substrate pyro-Glu-Pro-Arg-pNA (0.39 mM, S2366, Chromogenix) was added to a given amount of activated protein C (2 nM) previously incubated with or without the inhibitor under test (20° C., 30 minutes).

In order to assess in vitro the selectivity with respect to thrombin and plasmin, the same protocol was applied to purified human thrombin (0.7 nM, Sigma) and to purified human plasmin (2 nM, Stago), using as substrates purified human fibrinogen (6 μM, Enzyme Research Laboratories) and the paracitroanilide peptide <Glu-Phe-Lys-pNA (0.37 mM, S2403, Chromogenix), respectively.

The inhibitors, enzymes and substrates are diluted in the same buffer (0.01 mM phosphate buffer pH 7.4 containing 0.12M sodium chloride and 0.05% bovine serum albumin in the case of thrombin and 50 mM TRIS-HCl buffer pH 7.4 containing 0.12M sodium chloride, 3 mM calcium chloride and 0.05% bovine serum albumin in the case of activated protein C and plasmin) and then dispensed in a volume of 50 μl onto a polystyrene microplate.

The paranitroanilide liberated or the fibrin formed by the action of the serine protease is measured spectrophotometrically at 405 nm after reacting for from 10 to 30 minutes at 20° C.

In this test the compounds of the invention are powerful inhibitors of activated protein C (the concentration of compounds inhibiting 50% ($IC_{50}$) of the enzymatic activity being of the order of from 20 to 1000 nM).

The compounds moreover possess very marked selectivity with respect to a fibrinolysis serine protease, plasmin, and a coagulation serine protease, thrombin.

By way of example, the compound of Example 1 has an $IC_{50}$ of 820 nM with respect to activated protein C, of 1100 nM with respect to plasmin and of >33,000 nM with respect to thrombin.

EXAMPLE 77

Pharmaceutical Composition

Formula for the preparation of 1000 tablets each containing 10 mg of active ingredient:

| | |
|---|---|
| compound of Example 1 | 10 g |
| hydroxypropylcellulose | 2 g |
| wheat starch | 10 g |
| lactose | 100 g |
| magnesium stearate | 3 g |
| talc | 3 g |

The invention claimed is:

1. A compound selected from those of formula (I):

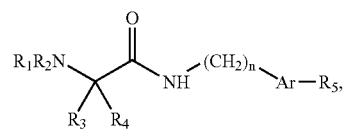

wherein:
$R_1$ represents aryl, heteroaryl or linear or branched ($C_1$-$C_6$)alkyl optionally substituted by one or more identical or different groups selected from aryl and heteroaryl, or $R_1$ represents a group of formula —(CO)—$CR_6R_7NR_8R_9$ wherein:
$R_6$ represents hydrogen or a group selected from aryl, heteroaryl, heterocycloalkyl, ($C_3$-$C_8$)cycloalkyl and linear or branched ($C_1$-$C_6$)alkyl optionally substituted by one or more identical or different groups selected from aryl, heteroaryl, heterocycloalkyl, ($C_3$-$C_8$)cycloalkyl and carboxy,
$R_7$ represents hydrogen or linear or branched ($C_1$-$C_6$) alkyl,
or $R_6$ and $R_7$ together form a ($C_3$-$C_8$)cycloalkyl group,
$R_8$ represents hydrogen or linear or branched ($C_1$-$C_6$) alkyl,
and $R_9$ represents hydrogen or $R'_9$ wherein $R'_9$ represents a group selected from
linear or branched ($C_1$-$C_6$)alkyl optionally substituted by aryl, carboxy, linear or branched ($C_1$-$C_6$) alkoxy-carbonyl or carbamoyl,
aryl,
heteroaryl,
and sulphonyl substituted by a group selected from ($C_3$-$C_8$)cycloalkyl, heterocycloalkyl, aryl (optionally substituted by aryloxy or heteroaryloxy), and linear or branched ($C_1$-$C_6$)alkyl optionally substituted by aryl, heteroaryl, ($C_3$-$C_8$)cycloalkyl or heterocycloalkyl,
$R_2$ represents hydrogen or linear or branched ($C_1$-$C_6$) alkyl,
$R_3$ represents hydrogen or linear or branched ($C_1$-$C_6$)alkyl optionally substituted by one or more aryl groups, $R_4$ represents a saturated or unsaturated, 7- to 15-membered bicyclic system or linear or branched $(C_1-C_6)$ alkyl optionally substituted by one or more aryl groups, or $R_3$ and $R_4$, together with the carbon atom carrying them, form a saturated or unsaturated, 3- to 18-membered, mono-, bi- or tri-cyclic system optionally containing one or more hetero atoms selected from O, S and N and optionally substituted by one or more identical or different groups selected from halogen, linear or branched $(C_1-C_6)$alkyl, linear or branched $(C_1-C_6)$alkoxy, hydroxy, linear or branched $(C_1-C_6)$ trihaloalkyl, amino (optionally substituted by one or more linear or branched $(C_1-C_6)$alkyl groups) and carboxy, n represents 1 or 2, Ar represents aryl or heteroaryl, $R_5$ represents a group selected from amino, guanidino, cyano and amidino optionally substituted by hydroxy or linear or branched $(C_1-C_6)$alkoxy-carbonyl, its optical isomers, and also addition salts thereof with a pharmaceutically acceptable acid, it being understood that:

heterocycloalkyl may be a 3- to 8-membered, saturated monocyclic group containing one, two or three hetero atoms selected from oxygen, nitrogen and sulphur, it being understood that the heterocycle may optionally be substituted by one or more identical or different groups selected from halogen, linear or branched $(C_1-C_6)$alkyl, linear or branched $(C_1-C_6)$alkoxy, oxo, hydroxy, linear or branched $(C_1-C_6)$trihaloalkyl and amino (optionally substituted by one or more linear or branched $(C_1-C_6)$alkyl groups), aryl may be phenyl, biphenylyl or naphthyl, each of those groups being optionally substituted by one or more identical or different groups selected from halogen, linear or branched $(C_1-C_6)$alkyl, linear or branched $(C_1-C_6)$alkoxy, hydroxy, linear or branched $(C_1-C_6)$ trihaloalkyl, and amino (optionally substituted by one or more linear or branched $(C_1-C_6)$alkyl groups), and heteroaryl may be a mono- or bi-cyclic, 5- to 12-membered, aromatic group containing one, two or three hetero atoms selected from oxygen, nitrogen and sulphur, it being understood that the heteroaryl may optionally be substituted by one or more identical or different groups selected from halogen, linear or branched $(C_1-C_6)$alkyl, hydroxy, linear or branched $(C_1-C_6)$alkoxy, trihalomethyl and amino (optionally substituted by one or more linear or branched $(C_1-C_6)$ alkyl groups).

2. A compound of claim 1, wherein $R_1$ represents a group of formula —(CO)—$CHR_6NHR_9$ wherein $R_6$ represents $(C_3-C_8)$cycloalkyl, or linear or branched $(C_1-C_6)$alkyl optionally substituted by $(C_3-C_8)$cycloalkyl, and $R_9$ represents a group selected from linear or branched $(C_1-C_6)$alkyl optionally substituted by carboxy, linear or branched $(C_1-C_6)$alkoxy-carbonyl or carbamoyl, and linear or branched $(C_1-C_6)$alkylsulphonyl substituted by $(C_3-C_8)$cycloalkyl.

3. A compound of claim 1, wherein $R_3$ and $R_4$, which may be the same or different, each represent linear or branched $(C_1-C_6)$alkyl.

4. A compound of claim 1, wherein $R_3$ and $R_4$ together form an optionally substituted indanyl group or a cyclopentapyridyl group.

5. A compound of claim 1, wherein n represents 1.

6. A compound of claim 1, wherein Ar represents phenyl and $R_5$ represents amidino optionally substituted by hydroxy.

7. A compound of claim 1, wherein Ar represents pyridyl substituted by methyl and $R_5$ represents amino.

8. A compound of claim 1, wherein $R_1$ represents a group of formula —(CO)—$CHR_6NR_8R_9$ wherein $R_6$, $R_8$ and $R_9$ are as defined for formula (I) and the centre of asymmetry composed of the carbon atom carrying the substituents $R_6$ and $NR_8R_9$ is of the R configuration.

9. A compound of claim 1, which is {[(1R)-2-({2-[({4-amidinobenzyl}-amino)-carbonyl]-indan-2-yl}-amino)-1-cyclohexyl-2-oxoethyl]-amino}acetic acid, its optical isomers, and also addition salts thereof with a pharmaceutically acceptable acid.

10. A compound of claim 1, which is ethyl {[(1R)-2-({2-[({4-[amino-(hydroxyimino)-methyl]-benzyl}-amino)-carbonyl]-indan-2-yl}-amino)-1-cyclohexyl-2-oxoethyl]-amino}-acetate, its optical isomers, and also addition salts thereof with a pharmaceutically acceptable acid.

11. A compound of claim 1, which is {[(1R)-2-({2-[({4-amidinobenzyl}-amino)-carbonyl]-indan-2-yl}-amino)-1-cyclohexylmethyl-2-oxoethyl]-amino}acetic acid, its optical isomers, and also addition salts thereof with a pharmaceutically acceptable acid.

12. A compound of claim 1, which is {[(1R)-2-({2-[({4-amidinobenzyl}-amino)-carbonyl]-indan-2-yl}-amino)-1-isopropyl-2-oxoethyl]-amino}acetic acid, its optical isomers, and also addition salts thereof with a pharmaceutically acceptable acid.

13. A compound of claim 1, which is N-(4-amidinobenzyl)-2-[((2R)-2-cyclohexyl-2-{[(cyclohexylmethyl)-sulphonyl]-amino}-ethanoyl)-amino]-2-indancarboxamide, its optical isomers, and also addition salts thereof with a pharmaceutically acceptable acid.

14. A compound of claim 1, which is N-(4-amidinobenzyl)-2-[((2R)-2-{[(cyclohexylmethyl)-sulphonyl]-amino}-3-methylbutanoyl)-amino]-2-indancarboxamide, its optical isomers, and also addition salts thereof with a pharmaceutically acceptable acid.

15. A compound of claim 1, which is N-(4-amidinobenzyl)-2-[((2R)-2-{[isobutylsulphonyl]-amino}-3-methylbutanoyl)-amino]-2-indancarboxamide, its optical isomers, and also addition salts thereof with a pharmaceutically acceptable acid.

16. A compound of claim 1, which is N-(4-amidinobenzyl)-6-[((2R)-2-5 {[(cyclohexylmethyl)-sulphonyl]-amino}-3-methylbutanoyl)-amino]-6,7-dihydro-5H-cyclopenta[b]pyridine-6-carboxamide, its optical isomers, and also addition salts thereof with a pharmaceutically acceptable acid.

17. A pharmaceutical composition comprising as active ingredient a compound of claim 1, together with one or more inert, non-toxic and pharmaceutically acceptable excipients or vehicles.

18. A method of treating a living animal body, including a human, afflicted with a disorder involving a dysfunction of haemostasis requiring procoagulant treatment, comprising the step of administering to the living animal body, including a human, an amount of a compound of claim 1 which is effective for alleviation of said disorder.

19. A method of treating a living animal body, including a human, afflicted with a condition requiring an antidote medicament in antithrombotic treatments, comprising the step of administering to the living animal body, including a human, an amount of a compound of claim 1 which is effective for alleviation of said condition.

* * * * *